US011407777B2

(12) United States Patent
Hironaka et al.

(10) Patent No.: US 11,407,777 B2
(45) Date of Patent: Aug. 9, 2022

(54) METAL-ORGANIC FRAMEWORK MANUFACTURING METHOD

(71) Applicant: FUJIFILM Corporation, Tokyo (JP)

(72) Inventors: Koji Hironaka, Kanagawa (JP); Masaya Nakayama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 95 days.

(21) Appl. No.: 17/020,839

(22) Filed: Sep. 15, 2020

(65) Prior Publication Data

US 2021/0002314 A1 Jan. 7, 2021

Related U.S. Application Data

(63) Continuation of application No. PCT/JP2019/012190, filed on Mar. 22, 2019.

(30) Foreign Application Priority Data

Mar. 22, 2018 (JP) ............................ JP2018-055077

(51) Int. Cl.

| | |
|---|---|
| ***C07F 15/02*** | (2006.01) |
| ***B01J 20/22*** | (2006.01) |
| ***B01J 20/30*** | (2006.01) |
| ***C01G 49/00*** | (2006.01) |
| ***C07C 51/41*** | (2006.01) |
| ***C07C 63/28*** | (2006.01) |
| ***C07C 245/06*** | (2006.01) |

(52) U.S. Cl.

CPC ............. *C07F 15/02* (2013.01); *B01J 20/226* (2013.01)

(58) Field of Classification Search

None

See application file for complete search history.

(56) References Cited

U.S. PATENT DOCUMENTS

2011/0172412 A1 7/2011 Serre et al.
2013/0129608 A1 5/2013 Watanabe et al.
2017/0166661 A1 6/2017 Liang et al.

FOREIGN PATENT DOCUMENTS

| | | | |
|---|---|---|---|
| AM | 1196 A2 * | 12/2002 | ............... C11D 3/37 |
| JP | 2001340754 | 12/2001 | |
| JP | 2006328050 | 12/2006 | |
| JP | 2006328051 | 12/2006 | |
| JP | 2006328051 A * | 12/2006 | .............. B01J 20/22 |
| JP | 2011524870 | 9/2011 | |
| JP | 2012006854 | 1/2012 | |
| JP | 2017522904 | 8/2017 | |

OTHER PUBLICATIONS

Lee et al., "Measurement of the dispersion stability of pristine and surface-modified multiwalled carbon nanotubes in various nonpolar and polar solvents." Meas. Sci. Technol., vol. 18 (2007), pp. 3707-3712.*

Mackie et al., "Studies in the Thermochemistry of Sulphoxides. Part 1.—The Gas-Phase Heats of Formation of Dethyl, Di-nPropyl, t-Butyl Ethyl, Allyl Ethyl and Diphenyl Sulphoxides." Trans. Faraday Soc. (1961), vol. 57, pp. 2119-2124.*

"Pressure-Temperature Nomograph Interactive Tool". Millipore Sigma, (c) 2022. Viewed on Feb. 15, 2022 at https://www.sigmaaldrich.com/US/en/support/calculators-and-apps/pressure-temperature-nomograph-interactive-tool.*

Maolin Pang et al., "Synthesis and Integration of Fe-soc-MOF Cubes into Colloidosomes via a Single-Step Emulsion-Based Approach", Journal of the American Chemical Society, Jul. 3, 2013, pp. 1-20.

"International Search Report (Form PCT/ISA/210) of PCT/JP2019/012190," dated Jun. 18, 2019, with English translation thereof, pp. 1-5.

"Written Opinion of the International Searching Authority (Form PCT/ISA/237) of PCT/JP2019/012190," dated Jun. 18, 2019, with English translation thereof, pp. 1-13.

"Office Action of Japan Counterpart Application" with English translation thereof, dated Aug. 24, 2021, p. 1-p. 12.

* cited by examiner

*Primary Examiner* — Daniel Berns

(74) *Attorney, Agent, or Firm* — JCIPRNET

(57) ABSTRACT

An object of the present invention is to provide a metal-organic framework manufacturing method of manufacturing a metal-organic framework having excellent gas adsorbability and durability.

A metal-organic framework manufacturing method according to an embodiment of the present invention includes: a step of mixing a metal salt containing a metal atom and a polydentate ligand in the presence of a solvent to manufacture a metal-organic framework, the polydentate ligand contains a compound represented by Formula (1), a content of the compound represented by Formula (1) in the polydentate ligand is 50 mol % or greater with respect to a total molar amount of the polydentate ligand, the solvent contains an organic solvent having a boiling point of 100° C. or higher, and a water content in the solvent is 0 to 90 mass % with respect to a total mass of the solvent.

(1)

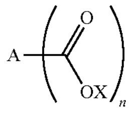

20 Claims, No Drawings

METAL-ORGANIC FRAMEWORK MANUFACTURING METHOD

CROSS-REFERENCE TO RELATED APPLICATIONS

This application is a Continuation of PCT International Application No. PCT/JP2019/012190 filed on Mar. 22, 2019, which claims priority under 35 U.S.C. § 119(a) to Japanese Patent Application No. 2018-055077 filed on Mar. 22, 2018. Each of the above applications is hereby expressly incorporated by reference, in its entirety, into the present application.

BACKGROUND OF THE INVENTION

1. Field of the Invention

The present invention relates to a metal-organic framework manufacturing method.

2. Description of the Related Art

Various studies have been conducted about metal-organic frameworks (MOFs) in which metal ions or metal clusters and polydentate ligands form a two- to three-dimensional coordination network.

For example, Examples in JP2017-522904A discloses that a metal-organic framework is formed by reacting terephthalic acid disodium salt and $EuCl_3.6H_2O$ or $TbCl_3.6H_2O$ in the presence of water as a solvent.

The metal-organic framework formed in JP2017-522904A is contrived for inclusion of biomolecules, and allows the biomolecules to exist with the terephthalic acid disodium salt, $EuCl_3.6H_2O$ or $TbCl_3.6H_2O$, and the solvent in the reaction for forming the metal-organic framework.

SUMMARY OF THE INVENTION

In recent years, a material capable of adsorbing a gas (for example, nitrogen gas, hydrogen gas, methane gas, etc.) has been desired.

The present inventors produced a metal-organic framework with reference to the manufacturing method described in JP2017-522904A to conduct studies about properties of the framework, and found that sufficient gas adsorbability and durability are not necessarily obtained.

Therefore, an object of the present invention is to provide a metal-organic framework manufacturing method of manufacturing a metal-organic framework having excellent gas adsorbability and durability.

The present inventors have conducted intensive studies to achieve the object, and as a result, found that in a case where a metal-organic framework is manufactured using predetermined materials under predetermined conditions, the object is achieved, and completed the present invention.

That is, the present inventors have found that the object can be achieved by the following configuration.

[1] A metal-organic framework manufacturing method comprising: a step of mixing a metal salt and a polydentate ligand in the presence of a solvent to manufacture a metal-organic framework, in which the polydentate ligand contains a compound represented by Formula (1) to be described later, a content of the compound represented by Formula (1) in the polydentate ligand is 50 mol % or greater with respect to a total molar amount of the polydentate ligand, the solvent contains an organic solvent having a boiling point of 100° C. or higher, and a water content in the solvent is 0 to 90 mass % with respect to a total mass of the solvent.

[2] The metal-organic framework manufacturing method according to [1], in which the water content is 0 to 50 mass % with respect to the total mass of the solvent.

[3] The metal-organic framework manufacturing method according to [1] or [2], in which a molecular weight of the compound represented by Formula (1) is 230 or greater.

[4] The metal-organic framework manufacturing method according to any one of [1] to [3], in which the compound represented by Formula (1) is a compound represented by Formula (2) to be described later.

[5] The metal-organic framework manufacturing method according to any one of [1] to [4] in which the metal salt contains an iron atom.

[6] The metal-organic framework manufacturing method according to any one of [1] to [5] in which the solvent contains two or more kinds of organic solvents having a boiling point of 100° C. or higher.

According to the present invention, it is possible to provide a metal-organic framework manufacturing method of manufacturing a metal-organic framework having excellent gas adsorbability and durability.

DESCRIPTION OF THE PREFERRED EMBODIMENTS

Hereinafter, the present invention will be described in detail.

Hereinafter, a metal-organic framework manufacturing method according to an embodiment of the present invention will be described in detail.

In this specification, a numerical value range expressed using "to" means a range including numerical values before and after "to" as a lower limit and an upper limit.

The features of the present invention are that a compound represented by Formula (1) to be described later is used as a polydentate ligand in the manufacturing of a metal-organic framework, a solvent used contains an organic solvent having a boiling point of 100° C. or higher, and a water content in the solvent is 0 to 90 mass % with respect to the total mass of the solvent.

The metal-organic framework is a material formed of a metal component selected from the group consisting of metal clusters and metal ions, and a ligand capable of coordinating with the metal component, and is usually a material in which the metal component as an inorganic material and the ligand are self-assembled and bound via a coordinate bond.

According to the manufacturing method according to the embodiment of the present invention, a metal-organic framework to be obtained has excellent gas adsorbability and durability.

The mechanism by which the above effects are obtained is not clear, but is presumed as follows.

In a case where a polydentate ligand having a carboxylate structure is used as in the above-described manufacturing method disclosed in JP2017-522904A, water is usually used as a main solvent to ensure the solubility of the polydentate ligand.

However, in a case where the main solvent is water, it is thought that the solubility of the intermediate of the metal-organic framework formed using a metal salt and a polydentate ligand in the solvent is low, and a metal-organic framework to be formed is precipitated from the solvent in a state in which the framework is not sufficiently grown.

According to the manufacturing method according to the embodiment of the present invention, it is thought that the solubility of the intermediate in the solvent is good, and as a result, a metal-organic framework having excellent gas adsorbability and durability is grown.

In addition, it is presumed that in a case where the molecular weight of the compound represented by Formula (1) to be described later is 230 or greater, the metal clusters or metal ions derived from the metal salt and the polydentate ligand are more gently integrated. As a result, a metal-organic framework having more excellent gas adsorbability and durability is obtained.

Hereinafter, first, materials used in the present manufacturing method will be described in detail.

Metal Salt

The metal salt is a raw material component capable of producing metal clusters or metal ions in the solvent.

The metal salt is not particularly limited, and examples thereof include metal chlorides, metal nitrates, metal acetates, metal sulfates, metal hydrogen sulfates, metal bromides, metal carbonates, metal phosphates, and derivatives thereof (for example, monohydrate derivatives and polyhydrate derivatives).

The metal atom contained in the metal salt is preferably a metal atom selected from the group consisting of Fe, Mg, Ca, Sr, Ba, Ti, Zr, Hf, V, Mn, Re, Ru, Os, Co, Rh, Ir, Ni, Pd, Pt, Cu, Zn, Cd, Hg, Si, Ge, Sn, and Pb, more preferably a metal atom selected from the group consisting of Ni, Mn, Fe, Zn, Ti, Zr, Co, and Cu, and even more preferably Fe (iron atom) or Co (cobalt atom).

Examples of the metal salt include zinc nitrate ($Zn(NO_3)_2.xH_2O$), titanium nitrate ($Ti(NO_3)_4.xH_2O$), cobalt nitrate ($Co(NO_3)_2.xH_2O$), iron nitrate (III) ($Fe(NO_3)_3.xH_2O$), iron nitrate (II) ($Fe(NO_3)_2.xH_2O$); zinc chloride ($ZnCl_2.xH_2O$), titanium chloride ($TiCl_4.xH_2O$), zirconium chloride ($ZrCl_4.xH_2O$), cobalt chloride ($CoCl_2.xH_2O$), iron chloride (III) ($FeCl_3.xH_2O$), iron chloride (II) ($FeCl_2.xH_2O$); zinc acetate ($Zn(CH_3COO)_2.xH_2O$), titanium acetate ($Ti(CH_3COO)_4.xH_2O$), zirconium acetate ($Zr(CH_3COO)_4.xH_2O$), cobalt acetate ($Co(CH_3COO)_2.xH_2O$), iron acetate (III) ($Fe(CH_3COO)_3.xH_2O$), iron acetate (II) ($Fe(CH_3COO)_2.xH_2O$); zinc sulfate ($ZnSO_4.xH_2O$), titanium sulfate ($Ti(SO_4)_2.xH_2O$), zirconium sulfate ($Zr(SO_4)_2.xH_2O$), cobalt sulfate ($CoSO_4.xH_2O$), iron sulfate (III) ($Fe_2(SO_4)_3.xH_2O$), iron sulfate (II) ($FeSO_4.xH_2O$); zinc hydroxide ($Zn(OH)_2.xH_2O$), titanium hydroxide ($Ti(OH)_4.xH_2O$), zirconium hydroxide ($Zr(OH)_4.xH_2O$), cobalt hydroxide ($Co(OH)_2.xH_2O$), iron hydroxide (III) ($Fe(OH)_3.xH_2O$), iron hydroxide (II) ($Fe(OH)_2.xH_2O$); zinc bromide ($ZnBr_2.xH_2O$), titanium bromide ($TiBr_4.xH_2O$), zirconium bromide ($ZrBr_4.xH_2O$), cobalt bromide ($CoBr_2.xH_2O$), iron bromide (III) ($FeBr_3.xH_2O$), iron bromide (II) ($FeBr_2.xH_2O$); zinc carbonate ($ZnCO_3.xH_2O$), cobalt carbonate ($CoCO_3.xH_2O$), and iron carbonate (III) ($Fe_2(CO_3)_3.xH_2O$). x is a number of 0 to 12.

As the metal salt, at least one selected from the group consisting of iron nitrate (III) ($Fe(NO_3)_3.xH_2O$), iron nitrate (II) ($Fe(NO_3)_2.xH_2O$), iron chloride (III) ($FeCl_3.xH_2O$), iron chloride (II) ($FeCl_2.xH_2O$), iron sulfate (III) ($Fe_2(SO_4)_3.xH_2O$), and iron sulfate (II) ($FeSO_4.xH_2O$) is preferable from the viewpoint of obtaining a metal-organic framework having more excellent gas adsorbability and durability. Among these, at least one selected from the group consisting of iron nitrate (III) ($Fe(NO_3)_3.xH_2O$), iron nitrate (II) ($Fe(NO_3)_2.xH_2O$), and iron chloride (III) ($FeCl_3.xH_2O$) is more preferable from the viewpoint of obtaining a metal-organic framework having further excellent gas adsorbability and durability. From the viewpoint of fluidity in the manufacturing process of the metal-organic framework, iron chloride (III) ($FeCl_3.xH_2O$) is even more preferable.

The metal salts may be used alone or in combination of two or more kinds thereof.

Polydentate Ligand

The polydentate ligand contains a compound represented by Formula (1).

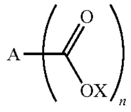

(1)

In Formula (1), n represents an integer of 2 to 6.

n is preferably 2 to 4, more preferably 3 or 4, and even more preferably 4 from the viewpoint that a metal-organic framework to be obtained has more excellent gas adsorbability and durability.

In addition, X represents Li, Na, K, or Cs.

X is preferably Na from the viewpoint that the metal-organic framework is more easily formed. A plurality of X's existing in Formula (1) may be the same or different from each other.

A represents an n-valent organic group.

The organic group represented by A is not particularly limited, and examples thereof include groups represented by (Y1) to (Y10). In (Y1) to (Y10), * represents a bonding position with —COOX (X: Li, Na, K, or Cs) shown in Formula (1).

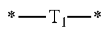

(Y1)

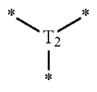

(Y2)

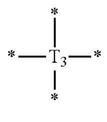

(Y3)

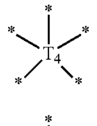

(Y4)

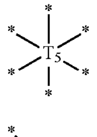

(Y5)

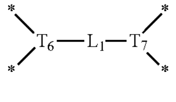

(Y6)

-continued (Y7)

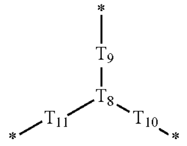

(Y8)

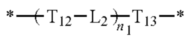

(Y9)

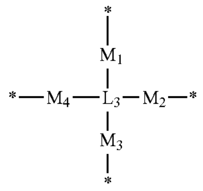

(Y10)

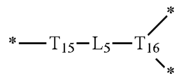

In (Y1) to (Y8) and (Y10), $T_1$, $T_9$, $T_{10}$, $T_{11}$, $T_{12}$, $T_{13}$, and $T_{15}$ represent a divalent aromatic hydrocarbon ring or a divalent aromatic heterocyclic ring, $T_2$, $T_6$, $T_7$, $T_8$, and $T_{16}$ each independently represent a trivalent aromatic hydrocarbon ring or a trivalent aromatic heterocyclic ring, $T_3$ represents a tetravalent aromatic hydrocarbon ring or a tetravalent aromatic heterocyclic ring, $T_4$ represents a pentavalent aromatic hydrocarbon ring or a pentavalent aromatic heterocyclic ring, and $T_5$ represents a hexavalent aromatic hydrocarbon ring or a hexavalent aromatic heterocyclic ring.

The number of carbon atoms contained in the aromatic hydrocarbon ring is preferably 6 to 18, more preferably 6 to 14, and even more preferably 6 to 10. The aromatic hydrocarbon ring may have a monocyclic structure or a condensed ring structure. Furthermore, the aromatic hydrocarbon ring may further have a substituent.

The aromatic heterocyclic ring is preferably a 5-, 6-, or 7-membered ring having at least one N atom, O atom, S atom, or Se atom in the ring structure, and more preferably a 5- or 6-membered ring. The aromatic heterocyclic ring may have a monocyclic structure or a condensed ring structure. Furthermore, the aromatic heterocyclic ring may further have a substituent.

In (Y6), $L_1$ represents a single bond or a divalent linking group.

Examples of the divalent linking group represented by $L_1$ include —N═N—, —O—, —S—, —$NR^a$—, —CO—, an alkylene group (which may be cyclic, branched, or linear), an alkenylene group, an alkynylene group, or a divalent group formed by combining the above groups. $R^a$ represents a hydrogen atom or a substituent (for example, an alkyl group).

In (Y8), $L_2$ represents a single bond or a divalent linking group.

Examples of the divalent linking group represented by $L_2$ include the same divalent linking group as those exemplified above for $L_1$.

In (Y8), $n_1$ represents an integer of 1 to 4.

In (Y8), * represents a bonding position.

In (Y9), $L_3$ represents a tetravalent linking group.

The tetravalent linking group represented by $L_3$ is not particularly limited, and examples thereof include a silicon atom, a carbon atom, a tetravalent alicyclic hydrocarbon ring, a tetravalent aromatic hydrocarbon ring, and a tetravalent aromatic heterocyclic ring.

The number of carbon atoms contained in the alicyclic hydrocarbon ring is preferably 6 to 18, more preferably 6 to 14, and even more preferably 6 to 10.

Examples of the tetravalent aromatic hydrocarbon ring or the tetravalent aromatic heterocyclic ring represented by $L_3$ include the same tetravalent aromatic hydrocarbon ring or tetravalent aromatic heterocyclic ring as those exemplified above for $T_3$.

In (Y9), $M_1$, $M_2$, $M_3$, and $M_4$ each independently represent a divalent linking group represented by Formula (A).

(A)

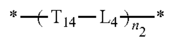

In Formula (A), $T_{14}$ represents a divalent aromatic hydrocarbon ring or a divalent aromatic heterocyclic ring.

Examples of the divalent aromatic hydrocarbon ring or the divalent aromatic heterocyclic ring represented by $T_{14}$ include the same divalent aromatic hydrocarbon ring or divalent aromatic heterocyclic ring as those exemplified above for $T_1$.

$L_4$ represents a single bond or a divalent linking group. Examples of the divalent linking group represented by $L_4$ include the same divalent linking group as those exemplified above for $L_1$.

$n_2$ represents an integer of 1 to 3.

* represents a bonding position.

In (Y10), $L_5$ represents a single bond or a divalent linking group.

Examples of the divalent linking group represented by $L_5$ include the same divalent linking group as those exemplified above for $L_1$.

In (Y10), * represents a bonding position.

The molecular weight of the compound represented by Formula (1) is not particularly limited, and is preferably 230 or greater, and more preferably 300 or greater from the viewpoint that a metal-organic framework to be obtained has more excellent gas adsorbability and durability. The upper limit is not particularly limited, and is preferably 1,500 or less.

Specific examples of the compound represented by Formula (1) are as follows.

Any of the following compounds may have a substituent.

Specific examples of the substituent include an alkyl group (preferably having 1 to 6 carbon atoms, and more preferably 1 to 3 carbon atoms), an alkoxy group (preferably having 1 to 6 carbon atoms, and more preferably 1 to 3 carbon atoms), a hydroxy group, a halogen atom (F, CI, Br, and I), and an amino group ($NH_2$).

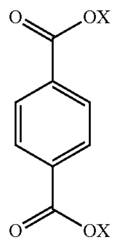

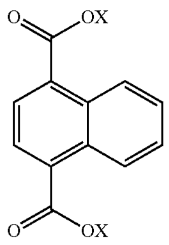

-continued
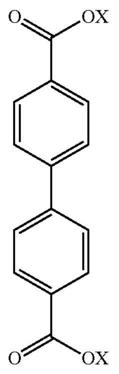
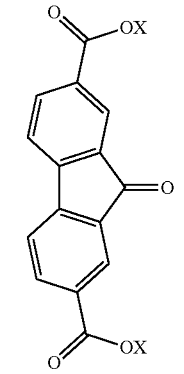
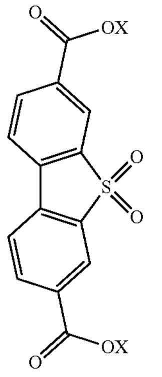
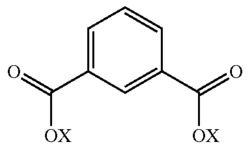
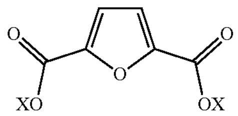
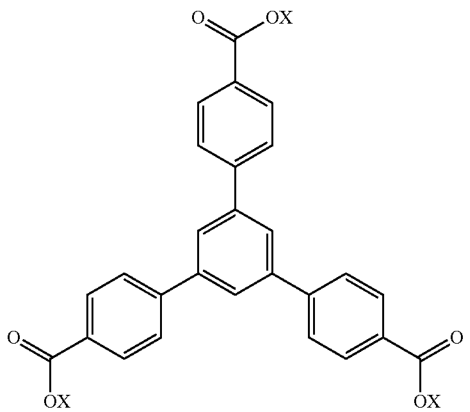
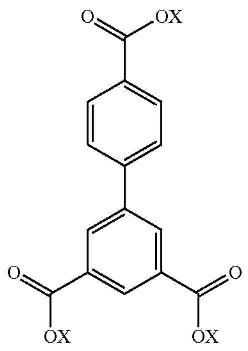
-continued
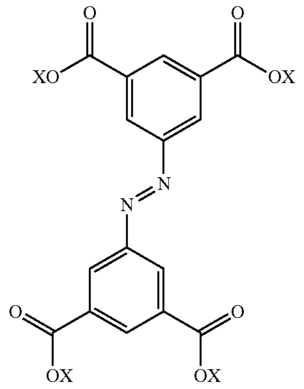
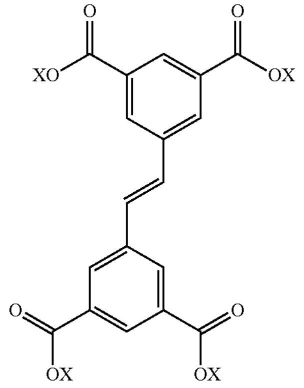
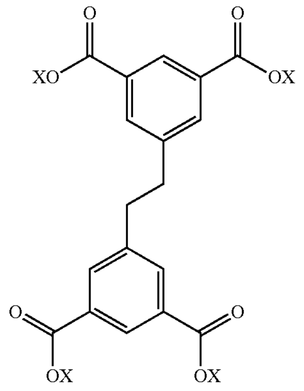
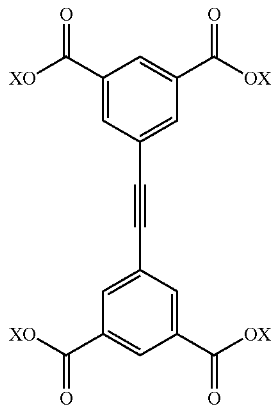
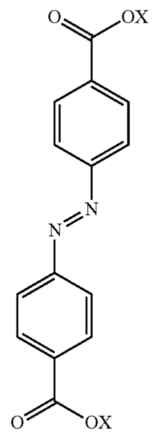

-continued
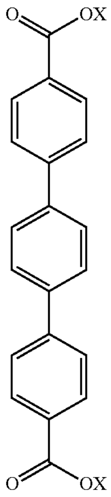
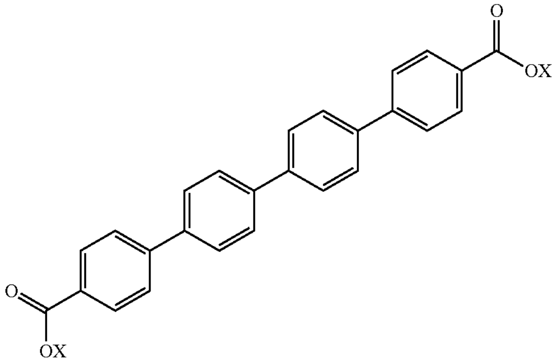
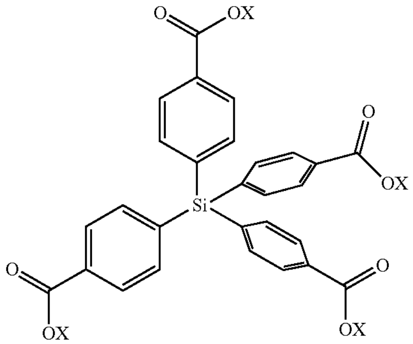
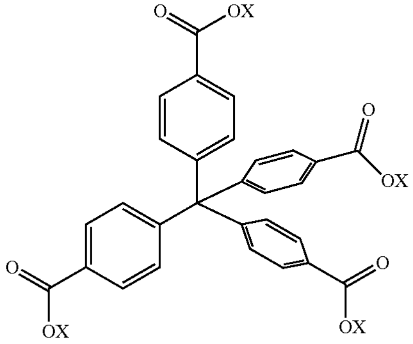
-continued
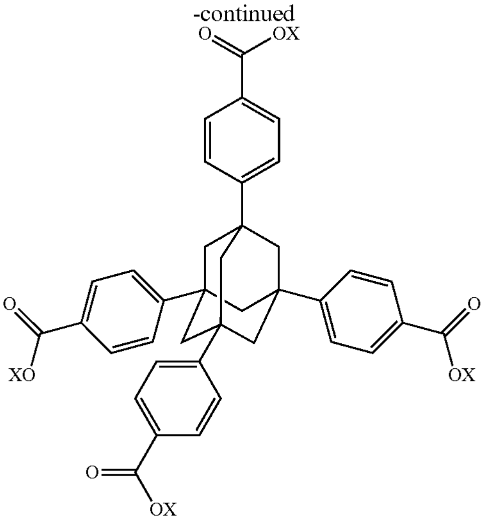
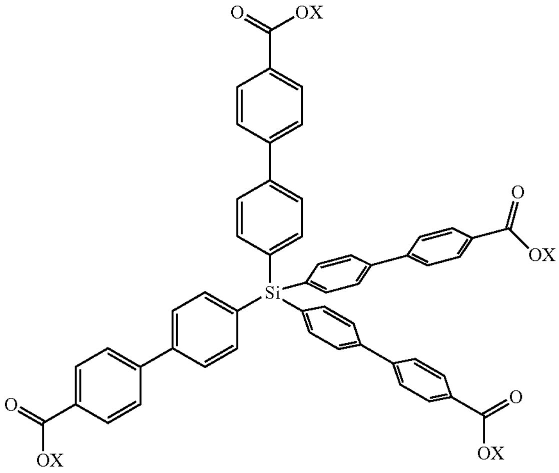
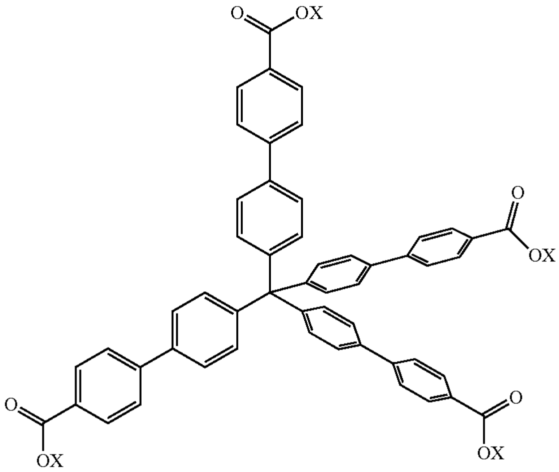

-continued

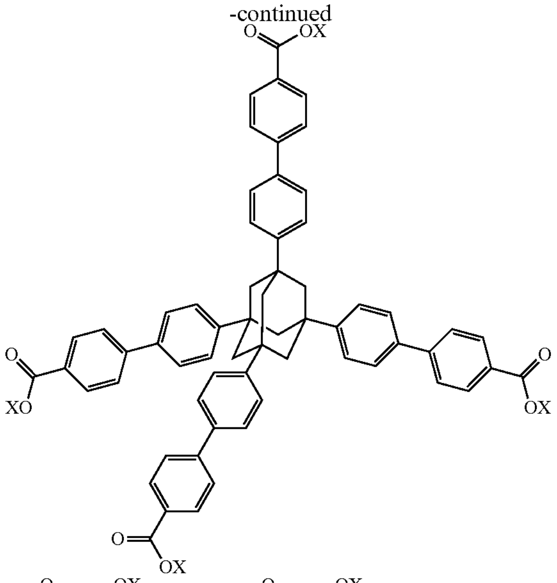

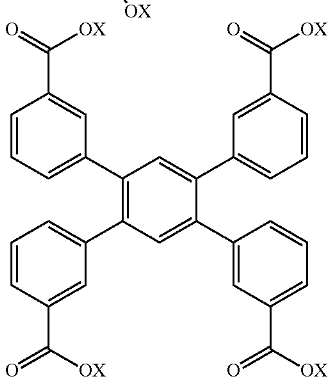

The compound represented by Formula (1) preferably has 2 to 8 benzene rings, more preferably 2 to 4 benzene rings, and even more preferably 2 benzene rings from the viewpoint that a metal-organic framework to be obtained has more excellent gas adsorbability and durability. In addition, the compound represented by Formula (1) preferably has 2 to 4 COOX moieties, more preferably 3 or 4 COOX moieties, and even more preferably 4 COOX moieties from the viewpoint that a metal-organic framework to be obtained has more excellent gas adsorbability and durability.

The compound represented by Formula (1) is preferably a compound represented by Formula (2) from the viewpoint that a metal-organic framework to be obtained has more excellent gas adsorbability and durability.

(2)

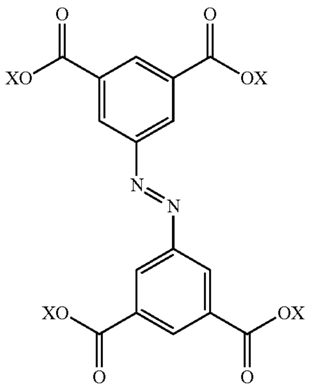

X in Formula (2) is synonymous with X in Formula (1), and preferable embodiments thereof are also the same.

The content of the compound represented by Formula (1) in the polydentate ligand is 50 mol % or greater with respect to the total molar amount of the polydentate ligand, and is more preferably 70 mol % or greater, and even more preferably 80 mol % or greater from the viewpoint that a metal-organic framework to be obtained has more excellent gas adsorbability and durability. The upper limit is not particularly limited, and may be 100 mol %.

The compounds represented by Formula (1) may be used alone or in combination of two or more kinds thereof.

The polydentate ligand may include a polydentate ligand other than the compound represented by Formula (1). Examples of other polydentate ligands include 4,4'-ethylenedipyridine, 4,4'-bipyridyl, pyrazine, 1,4-diazabicyclo[2.2.2]octane, terephthalic acid, and 4,4'-biphenyldicarboxylic acid. A compound in which a part or all of X in the compound represented by Formula (1) is substituted with a hydrogen atom may be contained as a polydentate ligand.

Solvent

The solvent contains an organic solvent having a boiling point of 100° C. or higher. The upper limit of the boiling point is not particularly limited, and is, for example, 300° C. or lower.

The boiling point means a boiling point under 1 atm.

The organic solvent having a boiling point of 100° C. or higher is not particularly limited, and examples thereof include DMF (N,N-dimethylformamide, boiling point: 153° C.), acetic acid (boiling point: 118° C.), DMSO (dimethyl sulfoxide, boiling point: 189° C.), ethylene glycol (boiling point: 197° C.), NMP (N-methylpyrrolidone, boiling point: 202° C.), NEP (N-ethylpyrrolidone, boiling point: 218° C.), DMAc (N,N-dimethylacetamide, boiling point: 165° C.), sulfolane (boiling point: 285° C.), 1,3-dimethyl-2-imidazolidinone (boiling point: 220° C.), propylene glycol (boiling point: 188° C.), 2-pyrrolidone (boiling point: 245° C.), diethylene glycol dimethyl ether (boiling point: 162° C.), diethylene glycol monoethyl ether acetate (boiling point: 218° C.), propylene glycol 1-monomethyl ether 2-acetate (boiling point 146° C.), and propylene glycol 1-monomethyl ether (boiling point: 120° C.).

The solubility parameter (SP) value of the organic solvent having a boiling point of 100° C. or higher is preferably 9 to 17 $(cal/cm^3)^{1/2}$, more preferably 10 to 16 $(cal/cm^3)^{1/2}$, and even more preferably 10 to 15 $(cal/cm^3)^{1/2}$. Examples of the organic solvent having an SP value of 9 to 17 $(cal/cm^3)^{1/2}$ and a boiling point of 100° C. or higher include acetic acid (12.6), DMF (12.0), and ethylene glycol (14.2).

Here, the solubility parameter of the solvent is defined by the Hildebrand's regular solution theory. More specifically, the solubility parameter of the solvent is a value $(cal/cm^3)^{1/2}$ defined by $(\Delta H\text{-}RT)N)^{1/2}$ where ΔH is molar evaporation heat of the solvent, V is a molar volume, R is a gas constant, and T is an absolute temperature.

Among these, two or more kinds of organic solvents having a boiling point of 100° C. or higher are preferably used in combination, an acetic acid and an organic solvent other than the acetic acid having a boiling point of 100° C. or higher are more preferably used in combination, an acetic acid and at least one selected from the group consisting of DMF, DMSO, propylene glycol 1-monomethyl ether, and ethylene glycol are even more preferably used in combination, an acetic acid and at least one selected from the group consisting of DMF, propylene glycol 1-monomethyl ether, and ethylene glycol are particularly preferably used in combination, and an acetic acid and DMF are most preferably used in combination from the viewpoint that a metal-organic framework to be obtained has more excellent durability.

The mixing ratio (mass ratio) of an acetic acid to an organic solvent other than the acetic acid having a boiling point of 100° C. or higher is preferably 10/90 to 90/10, more preferably 20/80 to 80/20, and even more preferably 30/70 to 70/30.

The solvent may contain a solvent other than the above-described organic solvent having a boiling point of 100° C. or higher.

Examples of other solvents include water and organic solvents having a boiling point of lower than 100° C. Examples of the organic solvent having a boiling point of lower than 100° C. include alcohol and ether.

The content of the organic solvent having a boiling point of 100° C. or higher in the solvent is preferably 20 mass % or greater, more preferably 30 mass % or greater, even more preferably 50 mass % or greater, particularly preferably 70 mass % or greater, and most preferably 90 mass % or greater with respect to the total mass of the solvent. The upper limit of the content of the organic solvent having a boiling point of 100° C. or higher is not particularly limited, and is 100 mass % with respect to the total mass of the solvent.

The content of the water in the solvent is 0 to 90 mass %, preferably 0 to 75 mass %, more preferably 0 to 50 mass %, and even more preferably 0 to 10 mass % with respect to the total mass of the solvent.

From the viewpoint of environment and cost, water is preferably used as the solvent, and water and an acetic acid are more preferably used in combination. In addition, the content of the water in the solvent is preferably 0 to 50 mass %, and more preferably 0 to 10 mass % from the viewpoint that a metal-organic framework to be obtained has more excellent gas adsorbability.

Procedures of Metal-Organic Framework Manufacturing Method

A metal-organic framework manufacturing method according to the embodiment of the present invention includes a step of mixing a metal salt and a polydentate ligand in the presence of a solvent to manufacture a metal-organic framework (hereinafter, also referred to as "step X").

The definitions of the metal salt, the polydentate ligand, and the solvent used in the step X are as described above.

An optimum mixing ratio of the metal salt to the polydentate ligand (number of moles of metal salt/number of moles of polydentate ligand) can be appropriately selected according to the kinds of the metal salt and the polydentate ligand to be used. The mixing ratio is, for example, preferably 1/1 to 5/1, and more preferably 2/1 to 4/1.

The mass percentage of the total content of the metal salt and the polydentate ligand with respect to the content of the solvent (total content of metal salt and polydentate ligand/content of solvent)×100, also referred to as "content A (mass %)" hereinbelow) is not particularly limited, and is preferably 0.5 mass % or greater, more preferably 1 mass % or greater, and even more preferably 3 mass % or greater. The upper limit is not particularly limited, and is preferably 30 mass % or less, and more preferably 20 mass % or less.

From the viewpoint of economic efficiency, it is also preferable that the content A is greater than 30 mass %. From the viewpoint of fluidity in the manufacturing process of the metal-organic framework, the content A is preferably 80 mass % or less, and more preferably 70 mass % or less.

The method of mixing the metal salt and the polydentate ligand is not particularly limited, and examples thereof include a method in which the metal salt and the polydentate ligand are added to the solvent, and the resulting solution is stirred.

The step X may be performed under heating conditions, and the heating temperature is not particularly limited, and is 100° C. or higher in many cases. The upper limit is not particularly limited. In many cases, the upper limit is usually 200° C. or lower. The heating time is not particularly limited, and from the viewpoint of productivity, the heating time is preferably 1 to 120 hours, and more preferably 3 to 48 hours.

Examples of the method of performing the heating treatment include a method in which a solution containing a metal salt, a polydentate ligand, and a solvent is put into a pressure-resistant container such as an autoclave, and pressurized at a high temperature, and a method in which a heating treatment is performed in the atmosphere using a heating device provided with a reflux tower.

The step X is preferably performed under an environment of 1 to 3 atm, and more preferably 1 atm (in the atmosphere).

The metal-organic framework manufacturing method according to the embodiment of the present invention may include a step other than the above-described step X.

Examples of other steps include a purification treatment for removing unreacted substances and a drying treatment.

Examples of the purification treatment include a washing treatment using a solvent. In the washing treatment, a solvent and a metal-organic framework may be brought into contact with each other, and examples thereof include a method in which a metal-organic framework is added to a solvent, and the resulting mixed liquid is optionally heat-treated.

Metal-Organic Framework

A metal-organic framework is manufactured by the above-described manufacturing method.

The metal-organic framework contains a metal component derived from a metal salt, which is selected from the group consisting of metal clusters and metal ions, and an organic component derived from a polydentate ligand. In the metal-organic framework, the metal component and the organic component are bonded via a coordinate bond, and nanopores having a certain size and arranged regularly are formed.

The metal component is a component derived from a metal salt, and is selected from the group consisting of metal clusters and metal ions. That is, examples thereof include metal clusters containing the metal atom contained in the metal salt and ions of the metal atom contained in the metal salt.

The metal cluster includes one or more metal ions. In addition, the metal cluster may further include one or more anions other than the metal ion.

From the viewpoint that metal clusters are easily formed, the metal ion is preferably a metal ion selected from the group consisting of $Mg^{2+}$, $Ca^{2+}$, $Sr^{2+}$, $Ba^{2+}$, $Ti^{4+}$, $Zr^{4+}$, $Hf^{4+}$, $V^{5+}$, $V^{4+}$, $V^{3+}$, $V^{2+}$, $Mn^{2+}$, $Re^{2+}$, $Fe^{3+}$, $Fe^{2+}$, $Ru^{3+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Zn^{2+}$, $Cd^{2+}$, $Hg^{2+}$, $Si^{2+}$, $Ge^{2+}$, $Sn^{2+}$, and $Pb^{2+}$, more preferably a metal ion selected from the group consisting of $Ni^{2+}$, $Mn^{2+}$, $Zn^{2+}$, $Ti^{4+}$, $Zr^{4+}$, $Co^{2+}$, $Fe^{3+}$, $Fe^{2+}$, and $Cu^{2+}$, and even more preferably a metal ion selected from the group consisting of $Co^{2+}$, $Fe^{3+}$, and $Fe^{2+}$.

Examples of the anion of the metal cluster include anions composed of non-metal elements of Groups 14 to 17 of the periodic table (long-form periodic table), and an anion composed of one or more elements of O, N, and S is preferable. The anion is preferably an anion selected from the group consisting of $O^{2-}$, $OH^-$, sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, sulfide, hydrogen sulfate, selenide, selenate, hydrogen selenate, telluride, tellurate, hydrogen tellurate, nitride, phosphide, arsenide, arsenate, hydrogen arsenate, dihydrogen arsenate, antimonide, antimonate, hydrogen antimonate, dihydrogen antimonate, fluoride, boride, borate, hydrogen borate, perchlorate, chlorite, hypochlorite, perbromate, bromite, hypobromite, periodate, and hypoiodite. $O^{2-}$, $OH^-$, or carbonate is more preferable from the viewpoint that metal clusters are easily formed.

As the metal cluster, a metal cluster represented by Formula (X) is preferable.

$M_pY_q$ Formula (X)

M represents a metal ion, and preferable metal ions are as described above. Y represents an anion composed of a non-metal element of Group 14, 15, 16, or 17 of the periodic table, and preferable anions are as described above. p represents an integer of 1 to 10. q represents an integer of 1 or more, and is preferably an integer of 1 to 10. q is adjusted such that the metal cluster has a predetermined charge.

Examples of the metal cluster include $FeO_6$, $Fe_3O$, $Zn_4O$, $AlO_6$, $Zn_2(CO_2)_4$, $Cu_2(CO_2)_4$, $CrO_6$, $Co_2(CO_2)_4$, $Zr_6O_4(OH)_4$, $Fe_2CoO$, $Ti_8O_8(OH)_4$, and $Zn_2O_2(CO_2)_2$.

The metal ion is not particularly limited, and examples thereof include those exemplified above for the metal ion contained in the metal cluster.

Examples of the organic component derived from the polydentate ligand include an organic component derived from the compound represented by Formula (1) described above, and more specific examples thereof include an anionic component in which X in Formula (1) is excluded.

Use

The metal-organic framework according to the embodiment of the present invention has excellent gas adsorbability and durability, and can thus be put to various uses. For example, it can be applied to a gas adsorbent.

The gas adsorbent can be applied to a gas separation device, a gas storage device, a sensor, and the like. For example, in a gas separation device including the gas adsorbent, the gas adsorbent may be applied as a material for a gas separation membrane. In a gas storage device including the gas adsorbent, the gas adsorbent may be applied to an adsorption portion. In a sensor including the gas adsorbent, for example, the gas adsorbent may be disposed on a cantilever type vibrator.

EXAMPLES

Hereinafter, the present invention will be described in more detail based on examples. Materials, used amounts, proportions, processing contents, processing orders, and the like shown in the following examples can be appropriately changed without departing from the spirit of the present invention. Therefore, the scope of the present invention should not be limitedly interpreted by the following examples.

Manufacturing of Metal-Organic Framework

Example 1

| (Composition A) | |
|---|---|
| $TazbNa_4$ | 93 g |
| (shown in Table 1, corresponding to a polydentate ligand) | |
| $Fe(NO_3)_3$•$9H_2O$ | 180 g |
| (corresponding to a metal salt) | |
| DMF | 1,888 g |
| (boiling point: 153° C., corresponding to an organic solvent having a boiling point of 100° C. or higher) | |
| Acetic Acid | 1,050 g |
| (boiling point: 118° C., corresponding to an organic solvent having a boiling point of 100° C. or higher) | |

Raw materials were put into a three-necked flask according to the composition A, and the obtained mixture was stirred at 145° C. for 6 hours in an open atmosphere to synthesize 70 g of a metal-organic framework PCN-250. PCN-250 is a metal-organic framework represented by $[Fe_3(\mu_3\text{-}O)(H_2O)_2(OH)(Tazb)_{3/2}]$, and Tazb has the following structure.

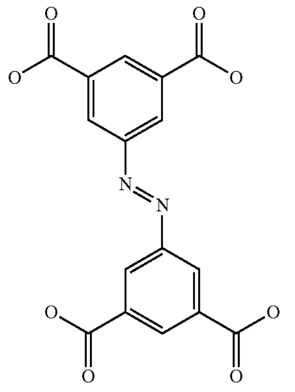 [SMILES: O=C(O)c1cc(/N=N/c2cc(C(=O)O)cc(C(=O)O)c2)cc(C(=O)O)c1]

95 g of water is contained in $TazbNa_4$ and $Fe(NO_3)_3 \cdot 9H_2O$ (corresponding to 3 mass % with respect to the total mass of the solvent).

Regarding 95 g of water, 72 g of water is in $Fe(NO_3)_3 \cdot 9H_2O$(moisture content: 40%), and 23 g of water is in $TazbNa_4$ (moisture content: 25%).

Masses of $TazbNa_4$ and $Fe(NO_3)_3.9H_2O$, excluding the water, are 70 g and 108 g, respectively.

Accordingly, the mass percentage of the total content of the metal salt and the polydentate ligand with respect to the content of the solvent ("content A (mass %)": represented by (total content of metal salt and polydentate ligand/content of solvent)×100) is calculated as follows:

| | |
|---|---|
| Metal Salt: $Fe(NO_3)_3 \bullet 9H_2O$ | 108 g |
| Polydentate Ligand: $TazbNa_4$ | 70 g |
| Solvent: DMF | 1,888 g |
| Acetic Acid | 1,050 g |
| Water (contained in the metal salt and the polydentate ligand) | 95 g |
| (108 + 70)/(1,888 + 1,050 + 95) × 100 = 6 mass % | |

Examples 2 to 6 and Comparative Examples 1 to 4

Metal-organic frameworks of Examples 2 to 6 and Comparative Examples 1 to 4 were manufactured in the same manner as in Example 1, except that various components and reaction conditions were changed as shown in the following Table 1.

Example 7

| (Composition B) | |
|---|---|
| $TazbNa_4$ (shown in Table 1, corresponding to a polydentate ligand) | 60 g |
| $Fe(NO_3)_3 \bullet 9H_2O$ (corresponding to a metal salt) | 116 g |
| DMF (boiling point: 153° C., corresponding to an organic solvent having a boiling point of 100° C. or higher) | 132 g |
| Acetic Acid (boiling point: 118° C., corresponding to an organic solvent having a boiling point of 100° C. or higher) | 74 g |

Raw materials were put into a three-necked flask according to the composition B, and the obtained mixture was stirred at 110° C. to 130° C. for 6 hours in an open atmosphere to synthesize a metal-organic framework PCN-250.

62 g of water is contained in $TazbNa_4$ and $Fe(NO_3)_3 \cdot 9H_2O$ (corresponding to 23 mass % with respect to the total mass of the solvent).

Regarding 62 g of water, 47 g of water is in $Fe(NO_3)_3 \cdot 9H_2O$ (moisture content: 40%), and 15 g of water is in $TazbNa_4$ (moisture content: 25%).

Masses of $TazbNa_4$ and $Fe(NO_3)_3.9H_2O$, excluding the water, are 45 g and 69 g, respectively.

Accordingly, the mass percentage of the total content of the metal salt and the polydentate ligand with respect to the content of the solvent ("content A (mass %)": represented by (total content of metal salt and polydentate ligand/content of solvent)×100) is calculated as follows:

| | |
|---|---|
| Metal Salt: $Fe(NO_3)_3 \bullet 9H_2O$ | 69 g |
| Polydentate Ligand: $TazbNa_4$ | 45 g |
| Solvent: DMF | 132 g |
| Acetic acid | 74 g |
| Water (contained in the metal salt and the polydentate ligand) | 62 g |
| (69 + 45)/(132 + 74 + 62) × 100 = 43 mass % | |

Example 8

| (Composition C) | |
|---|---|
| $TazbNa_4$ (shown in Table 1, corresponding to a polydentate ligand) | 90 g |
| $FeCl_3 \bullet 6H_2O$ (corresponding to a metal salt) | 116 g |
| DMF (boiling point: 153° C., corresponding to an organic solvent having a boiling point of 100° C. or higher) | 159 g |
| Acetic Acid (boiling point: 118° C., corresponding to an organic solvent having a boiling point of 100° C. or higher) | 81 g |

Raw materials were put into a three-necked flask according to the composition C, and the obtained mixture was stirred at 110° C. to 130° C. for 6 hours in an open atmosphere to synthesize a metal-organic framework PCN-250.

69 g of water is contained in $TazbNa_4$ and $FeCl_3.6H_2O$ (corresponding to 22 mass % with respect to the total mass of the solvent).

Regarding 69 g of water, 46 g of water is in $FeCl_3.6H_2O$ (moisture content: 40%), and 23 g of water is in $TazbNa_4$ (moisture content: 25%).

Masses of $TazbNa_4$ and $FeCl_3.6H_2O$, excluding the water, are 67 g and 70 g, respectively.

Accordingly, the mass percentage of the total content of the metal salt and the polydentate ligand with respect to the content of the solvent ("content A (mass %)": represented by (total content of metal salt and polydentate ligand/content of solvent)×100) is calculated as follows:

| | |
|---|---|
| Metal Salt: $FeCl_3 \bullet 6H_2O$ | 70 g |
| Polydentate Ligand: $TazbN_4$ | 67 g |
| Solvent: DMF | 159 g |
| Acetic acid | 81 g |
| Water (contained in the metal salt and the polydentate ligand) | 69 g |
| (70 + 68)/(159 + 81 + 69) × 100 = 44 mass % | |

Example 9

| (Composition D) | |
|---|---|
| $TazbNa_4$ (shown in Table 1, corresponding to a polydentate ligand) | 60 g |
| $FeCl_3•6H_2O$ (corresponding to a metal salt) | 77 g |
| DMF (boiling point: 153° C., corresponding to an organic solvent having a boiling point of 100° C. or higher) | 72 g |
| Acetic Acid (boiling point: 118° C., corresponding to an organic solvent having a boiling point of 100° C. or higher) | 36 g |

Raw materials were put into a three-necked flask according to the composition D, and the obtained mixture was stirred at 110° C. to 130° C. for 6 hours in an open atmosphere to synthesize a metal-organic framework PCN-250.

46 g of water is contained in $TazbNa_4$ and $FeCl_3.6H_2O$ (corresponding to 30 mass % with respect to the total mass of the solvent).

Regarding 46 g of water, 31 g of water is in $FeCl_3.6H_2O$ (moisture content: 40%), and 15 g of water is in $TazbNa_4$ (moisture content: 25%).

Masses of $TazbNa_4$ and $FeCl_3.6H_2O$, excluding the water, are 45 g and 46 g, respectively.

Accordingly, the mass percentage of the total content of the metal salt and the polydentate ligand with respect to the content of the solvent ("content A (mass %)": represented by (total content of metal salt and polydentate ligand/content of solvent)×100) is calculated as follows:

| | |
|---|---|
| Metal Salt: $FeCl_3•6H_2O$ | 46 g |
| Polydentate Ligand: $TazbNa_4$ | 45 g |
| Solvent: DMF | 72 g |
| Acetic Acid | 36 g |
| Water (contained in the metal salt and the polydentate ligand) | 46 g |
| (46 + 45)/(72 + 36 + 46) × 100 = 59 mass % | |

Example 10

| (Composition E) | |
|---|---|
| $TazbNa_4$ (shown in Table 1, corresponding to a polydentate ligand) | 25 g |
| $FeCl_2•4H_2O$ (corresponding to a metal salt) | 24 g |
| DMF (boiling point: 153° C., corresponding to an organic solvent having a boiling point of 100° C. or higher) | 38 g |
| Acetic Acid (boiling point: 118° C., corresponding to an organic solvent having a boiling point of 100° C. or higher) | 19 g |

Raw materials were put into a three-necked flask according to the composition E, and the obtained mixture was stirred at 110° C. to 130° C. for 6 hours in an open atmosphere to synthesize a metal-organic framework PCN-250.

15 g of water is contained in $TazbNa_4$ and $FeCl_2.4H_2O$ (corresponding to 21 mass % with respect to the total mass of the solvent).

Regarding 15 g of water, 9 g of water is in $FeCl_2.4H_2O$ (moisture content: 36%), and 6 g of water is in $TazbNa_4$ (moisture content: 25%).

Masses of $TazbNa_4$ and $FeCl_2.4H_2O$, excluding the water, are 19 g and 15 g, respectively.

Accordingly, the mass percentage of the total content of the metal salt and the polydentate ligand with respect to the content of the solvent ("content A (mass %)": represented by (total content of metal salt and polydentate ligand/content of solvent)×100) is calculated as follows:

| | |
|---|---|
| Metal Salt: $FeCl_2•4H_2O$ | 15 g |
| Polydentate Ligand: $TazbNa_4$ | 19 g |
| Solvent: DMF | 38 g |
| Acetic Acid | 19 g |
| Water (contained in the metal salt and the polydentate ligand) | 15 g |
| (15 + 19)/(38 + 19 + 15) × 100 = 47 mass % | |

Evaluation of Metal-Organic Framework

Evaluation of Gas Adsorbability

Using BELSORP-max (manufactured by MicrotracBEL Corp.), an $N_2$-adsorption quantity at 77 K was measured, and the $N_2$-adsorption quantity was evaluated according to the following criteria based on an adsorption quantity at 10 kPa. STP is an abbreviation for standard temperature and pressure.

Evaluation Criteria

"A": 300 ml (STP)/g or greater

"B": 200 ml (STP)/g or greater and less than 300 ml (STP)/g

"C": 100 ml (STP)/g or greater and less than 200 ml (STP)/g

"D": less than 100 ml (STP)/g

Evaluation of Durability

Each of the metal-organic frameworks of Examples 2 to 10 and Comparative Examples 1 to 4 was heat-treated at 150° C. for 5 hours in the atmosphere, and then adsorbability was evaluated in the same manner and according to the same criteria as in "Evaluation of Gas Adsorbability" described above.

The results are shown in Table 1.

In the tables, "content A (mass %)" means a mass percentage of the total content of the metal salt and the polydentate ligand with respect to the content of the solvent, and is represented by (total content of metal salt and polydentate ligand/content of solvent)×100.

TABLE 1
| | Polydentate Ligand | | | | | |
|---|---|---|---|---|---|---|
| | Compound Represented by Formula (1) | | | Other Compounds | | |
| | Kind | Molecular Weight | Content Based on Total Molar Amount of Polydentate Ligand (mol %) | Kind | Content Based on Total Molar Amount of Polydentate Ligand (mol %) | Metal Salt |
| Example 1 | 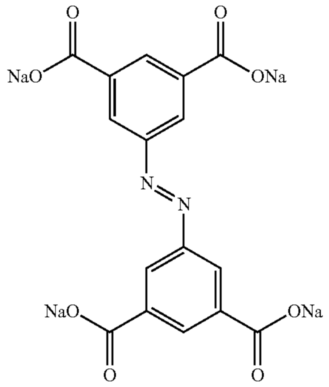 | 446 | 100 mol % | — | — | $Fe(NO_3)_3$•$9H_2O$ |
| Example 2 | 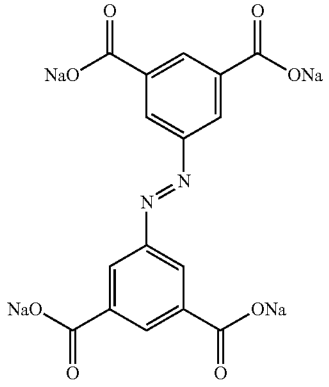 | 446 | 100 mol % | — | — | $Fe(NO_3)_3$•$9H_2O$ |
| Example 3 | 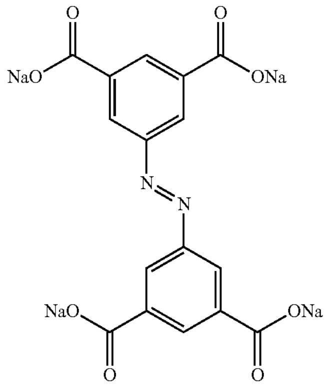 | 446 | 100 mol % | — | — | $Fe(NO_3)_3$•$9H_2O$ |
| Example 4 | 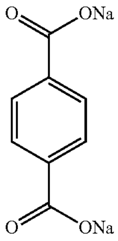 | 210 | 100 mol % | — | — | $FeCl_3$•$6H_2O$ |

TABLE 1-continued

| | | | | | | |
|---|---|---|---|---|---|---|
| Example 5 | 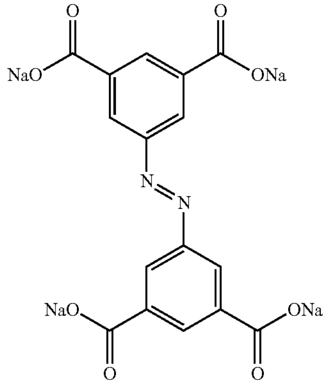 | 446 | 100 mol % | — | — | $Fe(NO_3)_3$•$9H_2O$ |

| | Solvent | | | | | | | | |
|---|---|---|---|---|---|---|---|---|---|
| | Water | Organic Solvent | | | | | | Evaluation | |
| | Content Based on Total Mass of Solvent | Kind | Boiling Point | Content Based on Total Mass of Solvent | Reaction Conditions | | | Gas Adsorption Performance | Durability |
| | | | | | Content A (mass %) | Pressure | Temperature | | |
| Example 1 | 3 mass % | DMF<br>Acetic Acid | 153° C.<br>118° C. | 62 mass %<br>35 mass % | 6 mass % | 1 atm | 140° C. to 150° C. | A | A |
| Example 2 | 30 mass % | Acetic Acid | 118° C. | 70 mass % | 6 mass % | 1 atm | 140° C. to 150° C. | A | B |
| Example 3 | 70 mass % | Acetic Acid | 118° C. | 30 mass % | 6 mass % | 1 atm | 140° C. to 150° C. | B | B |
| Example 4 | 49 mass % | DMF | 153° C. | 51 mass % | 6 mass % | 1 atm | 120° C. | C | C |
| Example 5 | 0 mass % | DMF<br>Acetic Acid | 153° C.<br>118° C. | 65 mass %<br>35 mass % | 6 mass % | 1 atm | 140° C. to 150° C. | A | A |

TABLE 2

| | Polydentate Ligand | | | | | |
|---|---|---|---|---|---|---|
| | Compound Represented by Formula (1) | | | Other Compounds | | |
| | Kind | Molecular Weight | Content Based on Total Molar Amount of Polydentate Ligand (mol %) | Kind | Content Based on Total Molar Amount of Polydentate Ligand (mol %) | Metal Salt |
| Example 6 | 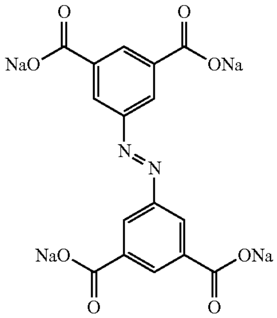 | 446 | 50 mol % | 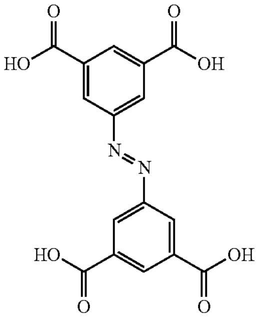 [SMILES: O=C(O)c1cc(/N=N/c2cc(C(=O)O)cc(C(=O)O)c2)cc(C(=O)O)c1] | — | $Fe(NO_3)_3$•$9H_2O$ |

TABLE 2-continued

| | | | | | | |
|---|---|---|---|---|---|---|
| Example 7 | 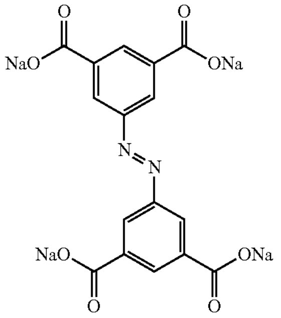 | 446 | 100 mol % | — | — | $Fe(NO_3)_3$•$9H_2O$ |
| Example 8 | 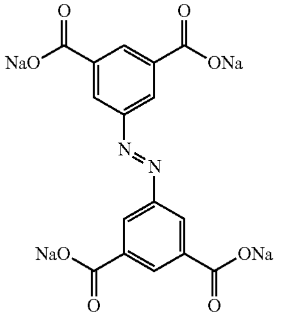 | 446 | 100 mol % | — | — | $FeCl_3$•$6H_2O$ |
| Example 9 | 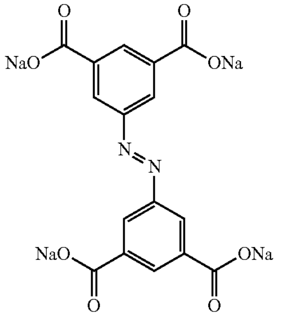 | 446 | 100 mol % | — | — | $FeCl_3$•$6H_2O$ |
| Example 10 | 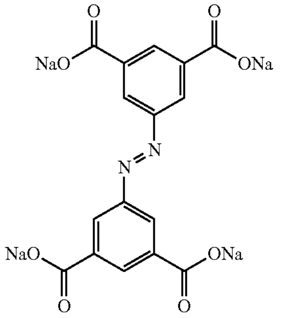 | 446 | 100 mol % | — | — | $FeCl_2$•$4H_2O$ |

| | Solvent | | | | | | | Evaluation | |
|---|---|---|---|---|---|---|---|---|---|
| | Water | Organic Solvent | | | Reaction Conditions | | | | |
| | Content Based on Total Mass of Solvent | Kind | Boiling Point | Content Based on Total Mass of Solvent | Content A (mass %) | Pressure | Temperature | Gas Adsorption Performance | Durability |
| Example 6 | 3 mass % | DMF<br>Acetic Acid | 153° C.<br>118° C. | 62 mass %<br>35 mass % | 6 mass % | 1 atm | 140° C. to 150° C. | A | A |

TABLE 2-continued

| | | | | | | | | | |
|---|---|---|---|---|---|---|---|---|---|
| Example 7 | 23 mass % | DMF Acetic Acid | 153° C. 118° C. | 49 mass % 28 mass % | 43 mass % | 1 atm | 110° C. to 130° C. | A | A |
| Example 8 | 22 mass % | DMF Acetic Acid | 153° C. 118° C. | 52 mass % 26 mass % | 44 mass % | 1 atm | 110° C. to 130° C. | A | A |
| Example 9 | 30 mass % | DMF Acetic Acid | 153° C. 118° C. | 47 mass % 23 mass % | 59 mass % | 1 atm | 110° C. to 130° C. | A | A |
| Example 10 | 21 mass % | DMF Acetic Acid | 153° C. 118° C. | 53 mass % 26 mass % | 47 mass % | 1 atm | 110° C. to 130° C. | B | B |

TABLE 3

| | Polydentate Ligand | | | | | |
|---|---|---|---|---|---|---|
| | Compound Represented by Formula (1) or Compound for Comparison | | | Other Compounds | | |
| | Kind | Molecular Weight | Content Based on Total Molar Amount of Polydentate Ligand (mol %) | Kind | Content Based on Total Molar Amount of Polydentate Ligand (mol %) | Metal Salt |
| Comparative Example 1 | 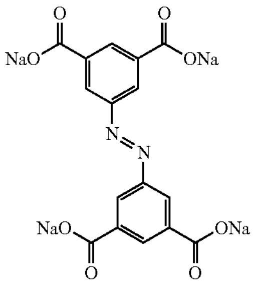 | 446 | 100 mol % | — | — | $Fe(NO_3)_3$•$9H_2O$ |
| Comparative Example 2 | 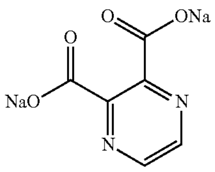 | 212 | 50 mol % | 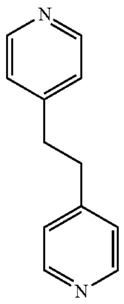 [SMILES: c1cc(CCc2ccncc2)ccn1] | 50 mol % | $Cu(ClO_4)_2$•$6H_2O$ |
| Comparative Example 3 | 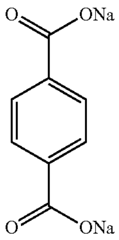 | 210 | 100 mol % | — | — | $FeCl_3$•$6H_2O$ |

TABLE 3-continued

| | | | | | | |
|---|---|---|---|---|---|---|
| Comparative Example 4 | 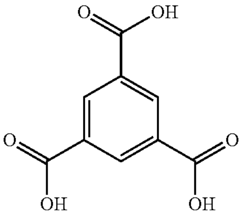 [SMILES: O=C(O)c1cc(C(=O)O)cc(C(=O)O)c1] | 210 | 100 mol % | — | — | $FeCl_3$•$6H_2O$ |

| | Solvent | | | | | | | Evaluation | |
|---|---|---|---|---|---|---|---|---|---|
| | Water | Organic Solvent | | | Reaction Conditions | | | Gas | |
| | Content Based on Total Mass of Solvent | Kind | Boiling Point | Content Based on Total Mass of Solvent | Content A (mass %) | Pressure | Temperature | Adsorption Performance | Durability |
| Comparative Example 1 | 100 mass % | — | — | — | 6 mass % | 1 atm | 100° C. | D | D |
| Comparative Example 2 | 44 mass % | Ethanol | 78° C. | 56 mass % | 6 mass % | 1 atm | Room Temperature | D | D |
| Comparative Example 3 | 100 mass % | — | — | — | 6 mass % | 1 atm | 80° C. | D | D |
| Comparative Example 4 | — | DMF | 153° C. | 100 mass % | 6 mass % | 1 atm | 140° C. to 150° C. | D | D |

From the results of Table 1, according to the manufacturing method of the examples, a metal-organic framework having excellent gas adsorbability and durability was obtained.

Comparing Example 1 with Examples 2 and 3, it has been confirmed that a metal-organic framework having more excellent durability is obtained in a case where the solvent contains two or more kinds of organic solvents having a boiling point of 100° C. or higher. Comparing Example 2 with Example 3, it has been confirmed that more excellent gas adsorbability is obtained in a case where the water content is 50 mass % or less with respect to the total solvent mass.

Comparing Example 2 with Example 4, it has been confirmed that a metal-organic framework having more excellent gas adsorbability and durability is obtained in a case where the molecular weight of the compound represented by Formula (1) is 230 or greater.

A metal-organic framework having excellent gas adsorbability and durability was also obtained in Examples 5 to 9 in the same manner as in Example 1. Comparing Example 1 with Examples 5 to 9, a slight reduction has been confirmed in adsorbability in Example 10 in which the metal salt was changed.

From the results of Comparative Examples 1 and 3, it has been confirmed that a metal-organic framework to be formed has poor gas adsorbability and durability in a case where the solvent consists only of water.

From the results of Comparative Example 2, it has been confirmed that a metal-organic framework to be formed has poor gas adsorbability and durability in a case where the solvent does not contain an organic solvent having a boiling point of 100° C. or higher.

From the results of Comparative Example 4, it has been confirmed that a metal-organic framework to be formed has poor gas adsorbability and durability in a case where the polydentate ligand does not have a metal salt structure.

What is claimed is:

1. A metal-organic framework manufacturing method comprising:

a step of mixing a metal salt and a polydentate ligand in the presence of a solvent to manufacture a metal-organic framework, wherein the polydentate ligand contains a compound represented by Formula (1), a content of the compound represented by Formula (1) in the polydentate ligand is 50 mol % or greater with respect to a total molar amount of the polydentate ligand, the solvent contains acetic acid and an organic solvent other than acetic acid having a boiling point of 100° C. or higher, and a water content in the solvent is 0 to 90 mass % with respect to a total mass of the solvent,

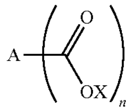

(1)

in the formula, n represents an integer of 2 to 6, A represents an n-valent organic group, X represents Li, Na, K, or Cs, and a plurality of X's may be the same or different from each other.

2. The metal-organic framework manufacturing method according to claim 1, wherein the water content is 0 to 50 mass % with respect to the total mass of the solvent.

3. The metal-organic framework manufacturing method according to claim 1, wherein a molecular weight of the compound represented by Formula (1) is 230 or greater.

4. The metal-organic framework manufacturing method according to claim 1, wherein the compound represented by Formula (1) is a compound represented by Formula (2), (2)

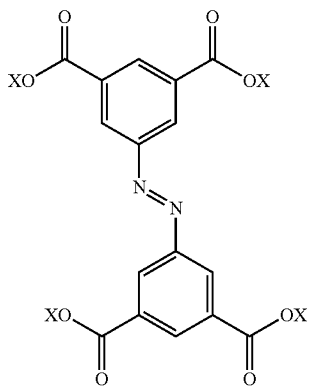

in the formula, X represents Li, Na, K, or Cs, and a plurality of X's may be the same or different from each other.

5. The metal-organic framework manufacturing method according to claim 1, wherein the metal salt contains an iron atom.

6. The metal-organic framework manufacturing method according to claim 1, wherein the solvent contains two or more kinds of organic solvents having a boiling point of 100° C. or higher.

7. The metal-organic framework manufacturing method according to claim 1, wherein at least one selected from the group consisting of $Fe(NO_3)_3.xH_2O$, $Fe(NO_3)_2.xH_2O$, and $FeCl_3.xH_2O$ is used as the metal salt, and x is a number of 0 to 12.

8. The metal-organic framework manufacturing method according to claim 2, wherein a molecular weight of the compound represented by Formula (1) is 230 or greater.

9. The metal-organic framework manufacturing method according to claim 2, wherein the compound represented by Formula (1) is a compound represented by Formula (2), (2)

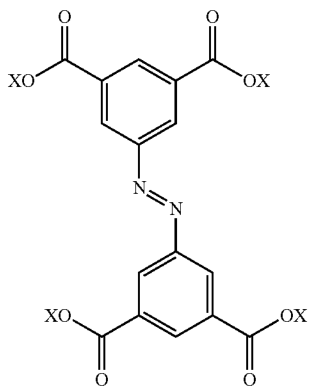

in the formula, X represents Li, Na, K, or Cs, and a plurality of X's may be the same or different from each other.

10. The metal-organic framework manufacturing method according to claim 2, wherein the metal salt contains an iron atom.

11. The metal-organic framework manufacturing method according to claim 2, wherein the solvent contains two or more kinds of organic solvents having a boiling point of 100° C. or higher.

12. The metal-organic framework manufacturing method according to claim 2, wherein at least one selected from the group consisting of $Fe(NO_3)_3.xH_2O$, $Fe(NO_3)_2.xH_2O$, and $FeCl_3.xH_2O$ is used as the metal salt, and x is a number of 0 to 12.

13. The metal-organic framework manufacturing method according to claim 3, wherein the compound represented by Formula (1) is a compound represented by Formula (2), (2)

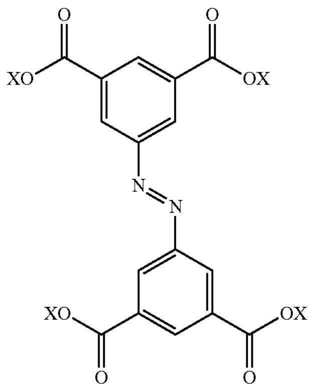

in the formula, X represents Li, Na, K, or Cs, and a plurality of X's may be the same or different from each other.

14. The metal-organic framework manufacturing method according to claim 3, wherein the metal salt contains an iron atom.

15. The metal-organic framework manufacturing method according to claim 3, wherein the solvent contains two or more kinds of organic solvents having a boiling point of 100° C. or higher.

16. The metal-organic framework manufacturing method according to claim 3, wherein at least one selected from the group consisting of $Fe(NO_3)_3.xH_2O$, $Fe(NO_3)_2.xH_2O$, and $FeCl_3.xH_2O$ is used as the metal salt, and x is a number of 0 to 12.

17. The metal-organic framework manufacturing method according to claim 4, wherein the metal salt contains an iron atom.

18. The metal-organic framework manufacturing method according to claim 4, wherein the solvent contains two or more kinds of organic solvents having a boiling point of 100° C. or higher.

19. The metal-organic framework manufacturing method according to claim 4, wherein at least one selected from the group consisting of $Fe(NO_3)_3.xH_2O$, $Fe(NO_3)_2.xH_2O$, and $FeCl_3.xH_2O$ is used as the metal salt, and x is a number of 0 to 12.

20. The metal-organic framework manufacturing method according to claim 5, wherein the solvent contains two or more kinds of organic solvents having a boiling point of 100° C. or higher.

* * * * *